United States Patent [19]

Dunn et al.

[11] Patent Number: 5,145,866

[45] Date of Patent: Sep. 8, 1992

[54] METHOD OF TREATING ANXIETY WITH THE AID OF R(+)-3-AMINO-1-HYDROXY-PYRROLIDIN-2-ONE

[75] Inventors: Robert W. Dunn, Warren; Roy Corbett, Bridgewater, both of N.J.

[73] Assignee: Hoechst-Roussel Pharmaceuticals Incorporated, Somerville, N.J.

[21] Appl. No.: 688,232

[22] Filed: Apr. 22, 1991

[51] Int. Cl.$^5$ .............................. A61K 31/40
[52] U.S. Cl. ................................... 514/425
[58] Field of Search ........................ 514/425

[56] References Cited

U.S. PATENT DOCUMENTS 3,167,476 1/1965 Bonta .................................. 167/65
4,863,953 9/1989 Leeson et al. ...................... 514/425

OTHER PUBLICATIONS

Coll. Czech. Chem. Comm., 1959, 24, 1672–1676, Smrt et al.
L. Singh et al., Proc. Natl. Acad. Sci., Jan. 1990, vol. 87, 347–351.
V. Macmillan, Brain Research, 146 (1978), 177–187.

*Primary Examiner*—Mary C. Lee
*Assistant Examiner*—Joseph K. McKane
*Attorney, Agent, or Firm*—Elliott Korsen

[57] ABSTRACT

A method of treating anxiety with the aid of R(+)-3-amino-1-hydroxypyrrolidin-2-one of the formula

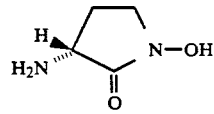

is disclosed.

2 Claims, No Drawings

METHOD OF TREATING ANXIETY WITH THE AID OF R(+)-3-AMINO-1-HYDROXY-PYRROLIDIN-2-ONE

This invention relates to a method of treating anxiety utilizing R(+)-3-amino-1-hydroxy-pyrrolidin-2-one.

No disclosure of the use of R(+)-3-amino-1-hydroxy-pyrrolidin-2-one for treating anxiety is known. However, its use as a neuroprotective agent is disclosed in U.S. Pat. No. 4,863,953. This patent also discloses the title compound's use for the treatment and/or prevention of convulsions.

The compound 3-amino-1-hydroxypyrrolidin-2-one is disclosed in *Coll. Czech. Chem. Comm.*, 1959, 24, 1672 and its use in the treatment of epilepsy and Parkinson's disease is described in British Pat. No. 1,041,861. That compound, known as HA-966, has also been described as being able to antagonize selectively N-methyl-D-aspartate (NMDA)-induced excitation (Evans et al., *Brain Research*, 1978, 148, 536–42).

The optical isomers of HA-966, designated as R(+) and S(−) and the racemate (±)HA-966 have been found to exhibit a dissociation of properties with regard to NMDA receptor antagonistic activity. That is, the R(+) isomer exhibits this activity without muscle relaxation or ataxia effect while the S(−) isomer exhibits all of the undesirable side effects.

It has now been found that the R(+) isomer and the (±) racemate are effective compounds for the treatment of anxiety. The S(−) isomer, as above, has been found to be less effective in this utility.

R(+) HA-966, a strychnine-insensitive glycine antagonist, has shown potential therapeutic efficacy in anxiety without some of the undesirable side effects of the competitive and non-competitive NMDA antagonists such as (±)-3-(2-carboxypiperazin-4-yl)-propyl-1-phosphonic acid (CPP) or (±)-5-methyl-10,11-dihydroxy-5H-dibenzo(a,d) cyclohepten-5,10-imine oxalate (MK 801) and diazepam. These side effects include muscle relaxation, memory impairment and ataxia. Additionally, R(±) HA-966 does not produce sedation or interact with alcohol.

The present invention particularly provides a method for treating anxiety which comprises administering to a patient a compound of the formula

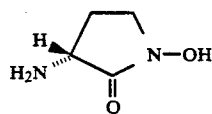

This compound may be useful for the treatment of anxiety which can manifest itself in the following physiological concomitants: increased heart rate, altered respiration rate, sweating, trembling, weakness and fatigue. Psychological concomitants of anxiety include feelings of impending danger, powerlessness, apprehension and tension.

EMBODIMENTS OF THE INVENTION

The present invention requires administration of a dose of the compound effective to treat anxiety. Thus, the dose required in accordance with the present invention is sufficiently great so as to permit the relief of the anxiety. Effective quantities of the compounds of the invention may be administered to a patient by any of the various methods, for example, orally as in capsules or tablets or parenterally, i.e., intravenously, intramuscular, in the form of sterile solutions or suspensions.

The dosage regimen for the compound in accord with this invention will depend on a variety of factors, including the type, age, weight, sex and medical condition of the patient.

The relief of anxiety may be achieved when R(+)-3-amino-1-hydroxypyrrolidin-2-one is administered to a subject requiring such treatment as an effective oral or parenteral dose of from about 0.1 to 1.5 mg/kg of body weight per day. A particularly effective amount is about 0.75 mg/kg of body weight per day. It is to be understood that for any particular subject, specific dosage regimens should be adjusted accordingly to the individual need and the professional judgement of the person administering or supervising the administration of the aforesaid compound. It is to be further understood that the dosages set forth herein are exemplary only and that they do not, to any extent, limit the scope or practice of the invention.

The compounds used in the method of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds used in the method of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The efficacy of R(+)-3-amino-1-hydroxypyrrolidin-2-one for the treatment of anxiety is demonstrated by its activity in the following animal test models.

SOCIAL INTERACTION TEST

For this test, naive male Wistar rats were housed in pairs for 10 days prior to the start of the test. Groups of six pairs of rats were suitable for each experimental condition as variability (standard error of the mean) between each pair of rats and sensitivity to drug effects within groups of rats was less than 15% from the mean. The social interaction test consisted of acclimating each pair (cagemates) of rats (250-300 g) to the arena 50×50×30 cm for a period of 8 min on two consecutive days. On the third day, each rat was randomly assigned according to weight to an unfamiliar partner in groups of 12 animals (six pairs) which were subsequently administered i.p. (1 ml/kg) the test drug. These rats were then replaced into their home cage with their original cagemate until testing. Following a 30 minute pretreatment time, each pair of unfamiliar rats was placed in the test arena and observed for social interaction behavior and overall motor activity for 5 minutes with a summed score totalled for each parameter per pair of rats. Social interaction time (sec) per pair of rats was measured as time spent sniffing partner, climbing over and crawling under partner, mutual grooming, genital investigation and following and walking around partner. Agressive behavior (biting, boxing, and pulling each other) was not considered as a social interaction behavior. Also, passive social contact was not counted as social interaction, i.e. if the animals were next to each other for more than 10 seconds and did not actively interact, the scoring was discontinued until movement resumed. Motor activity was measured by counting the number of rears (lifting of both front paws) and walks (of one body length) per pair of rats. (Ref.: Gardner, C. and Guy, Y.: A social interaction model of anxiety sensitive to acutely administered benzodiazepines. *Drug Dev. Res.* 4: 207-216, 1984.)

ELEVATED PLUS MAZE

For this test, male Wistar rats were also housed in pairs, for 10 days prior to testing in the apparatus. During this time the rats were handled by the investigator on alternate days to reduce stress. Groups consisted of 8 rats for each experimental condition as variability (standard error of the mean) between rats and sensitivity to drug effects was less than 15%. The day prior to testing in the elevated plus maze procedure, rats (200-250 g) were acclimated to the laboratory test room for 30 minutes and handled by the experimenter for 5 minutes. The maze, elevated to a height of 50 cm, consisted of two open arms 50×10 cm, and two enclosed arms 50×10×30 cm, arranged such that the two arms of each type were opposite each other. On the test day, drugs were administered i.p. (1 ml/kg) with a 30 minute pretreatment time and the rats were placed in the center of the maze, facing one of the enclosed arms. During a 5 minute test period, the following measures were taken by an observer: the number of entries into, and time spent in open and enclosed arms; and the total number of arm entries. Both the social interaction and the elevated plus maze procedures were conducted in a sound attenuated room, with observations made in an adjacent room via a remote control TV camera. (Ref.: Pellow, S. and File, S. E.; Anxiolytic and anxiogenic drug effects on exploratory activity in an elevated plus-maze; a novel test of anxiety in rats. (*Pharmacol. Biochem. Behav.* 24: 525-529, 1986.)

COOK AND DAVIDSON CONFLICT TEST

Male Wistar rats were trained for 6-8 weeks for this procedure. Approximately 60% of animals reached the criteria established for stable colony responding i.e., 2-7 conflict responses per session and stable Variable Interval (VI) responding with less than 10% variation from baseline. In order to achieve stable conflict responding, each rat was individually titrated to a shock level between 0.3-0.7 mA. As a result there was a low within subject variability in conflict responding, but a large between subject variability in VI control responding and in drug sensitivity, so that drug dosage was titrated for each individual subject. The Cook and Davidson conflict test was conducted in operant conditioning chambers consisting of a plexiglas cubicle (25×25×25 cm) with a stainless steel grid floor and aluminum front panel. The chamber was enclosed in a sound and light attenuating cubicle with white noise to mask extraneous sound and equipped with a ventilating fan. The response key was mounted on the front aluminum panel 5 cm above the grid floor and 5 cm from the plexiglas side wall. Sweetened condensed milk (40 $\mu$l) was presented by a dipper following bar press behavior from a well behind the midline of the front panel 3 cm above the grid floor. Recording equipment was located in an adjacent room. Sessions were conducted Monday through Friday and drugs were administered i.p. (1 ml/kg) with a 30 minute pretreatment time before the session on either Tuesday or Friday, if response rates were stable on the preceding control day.

The test parameters for the Cook and Davidson procedure were as follows. Food deprived rats (300-350 g) were trained to lever press for milk reward during two distinct periods, six VI-30 sec (no shock) periods lasting 4 minutes each alternating with six Fixed Ratio (FR-5) conflict periods lasting 3 minutes each during which every fifth bar press was followed by a milk reward and simultaneously a low level food shock (0.3-0.7 mA) to minimize bar pressing to 2-7 shocks per control session. (Ref.: Cook, L. and Davidson, A. B.: Effects of behaviorally active drugs in a conflict-punishment procedure in rats. The Benzodiazepines, ed. by S. Gratini et al., pp. 327-333, Raven Press, New York, 1973.)

STATISTICS

For the social interaction and elevated plus maze assays, data was analyzed by a one-way ANOVA followed by Dunnett's test to compare group drug effects to vehicle control behavior. Statistical analysis for the Cook and Davidson conflict procedure was by a dependent Student's t-test comparing an animal's previous day control behavior to the behavior following drug administration.

Results of the racemate (±)HA-966, R(+)HA-966 and S(−) HA-966 as well as diazepam for the three assays are given below in Tables 1, 2 and 3.

TABLE 1

Cook and Davidson Conflict

The effects of (±)HA-966, R(+)HA-966, S(−)HA-966 and diazepam in the Cook and Davidson conflict procedure. Rats were administered compounds (mg/kg, i.p.) 30 minutes prior to testing. Conflict responding was measured as mean number of shocks received (mean±S.E.) per session. N=7 animals per group.

TABLE 2

Social Interaction Test

The effects of (±)HA-966, R(+)-HA-966, S(−)-HA-966 and diazepam in the social interaction test. Rats were administered (mg/kg i.p.) compounds 30 minutes prior to testing. Social interaction behavior was measured in seconds (mean±S.E.) over 5 minutes. Motor activity was measured in activity units (mean±S.E.) equal to rearing and/or movement of one body length. N=6 pairs per group.

TABLE I

| | | COOK AND DAVIDSON CONFLICT PROCEDURE | | | |
|---|---|---|---|---|---|
| Compound | Dose (mg/kg) | VI Responding X ± S.E. | % Change | Conflict Rewards X ± S.E. | % Change |
| R(+)HA-966 | Veh. | 457.5 ± 101.9 | — | 3.0 ± 0.5 | — |
| | 10.0 | 384.5 ± 106.2 | −16 | 3.5 ± 0.4 | +17 |
| | Veh. | 335.4 ± 58.2 | — | 3.4 ± 0.4 | — |
| | 17.3 | 322.8 ± 97.2 | −4 | 3.1 ± 0.9 | −8 |
| | Veh. | 354.6 ± 56.6 | — | 3.1 ± 0.6 | — |
| | 30.0 | 92.6 ± 32.9 | −74 | 10.3 ± 1.7 | +226 |
| | Veh. | 528.7 ± 134.3 | — | 3.0 ± 0.7 | — |
| | 52.0 | 369.0 ± 118.2 | −30 | 10.7 ± 2.1 | +258 |
| (±)HA-966 | Veh. | 406.0 ± 88.9 | — | 4.3 ± 0.8 | — |
| | 0.3 | 494.3 ± 112.7 | −22 | 5.9 ± 1.0 | +37 |
| | Veh. | 595.6 ± 112.3 | — | 5.1 ± 0.5 | — |
| | 1.0 | 527.4 ± 150.7 | −11 | 13.0 ± 4.8 | +153 |
| | Veh. | 697.7 ± 177.8 | — | 3.4 ± 0.4 | — |
| | 3.0 | 492.6 ± 91.5 | −29 | 8.3 ± 1.9 | +142 |
| | Veh. | 537.8 ± 157.8 | — | 5.6 ± 0.7 | — |
| | 10.0 | ND | | ND | |
| S(−)HA-966 | Veh. | 404.3 ± 86.5 | — | 4.0 ± 0.7 | — |
| | 1.0 | 526.5 ± 107.2 | +30 | 5.2 ± 1.0 | +30 |
| | Veh. | 409.3 ± 109.6 | — | 3.2 ± 0.3 | — |
| | 3.0 | 301.5 ± 184.7 | −26 | 3.5 ± 1.3 | +11 |
| | Veh. | 441.6 ± 109.6 | — | 2.7 ± 0.2 | — |
| | 10.0 | 78.1 ± 74.8 | −82 | 0.8 ± 0.7 | −64 |
| Diazepam | Veh. | 321.6 ± 124.7 | — | 3.0 ± 0.55 | — |
| | 3.0 | 471.8 ± 126.2 | +47 | 9.8 ± 2.3 | +227 |
| | Veh. | 600.0 ± 125.5 | — | 4.7 ± 0.9 | — |
| | 10.0 | 809.9 ± 196.0 | +35 | 36.9 ± 8.9 | +682 |
| | Veh. | 516.6 ± 117.0 | — | 3.6 ± 0.6 | — |
| | 30.0 | 617.9 ± 165.6 | +19 | 27.1 ± 8.8 | +660 |

TABLE 2

| | | SOCIAL INTERACTION TEST | | | |
|---|---|---|---|---|---|
| Compound | Dose (mg/kg) | Social Interaction X ± S.E. (s) | % Change | Motor Activity X ± S.E. (Act. Units) | % Change |
| R(+)HA-966 | Veh. | 97.0 ± 3.1 | — | 159.6 ± 3.2 | — |
| | 1.0 | 95.1 ± 4.7 | −2 | 144.0 ± 7.2 | −10 |
| | 3.0 | 119.7 ± 3.4 | +23 | 158.8 ± 6.8 | −1 |
| | 10.0 | 126.7 ± 4.0 | +31 | 155.2 ± 5.2 | −3 |
| (±)HA-966 | Veh. | 94.6 ± 3.2 | — | 154.2 ± 5.5 | — |
| | 0.3 | 108.2 ± 1.2 | +14 | 150.3 ± 5.8 | −2 |
| | 1.0 | 121.8 ± 5.4 | +29 | 160.3 ± 3.7 | +4 |
| | 3.0 | 122.5 ± 2.9 | +31 | 141.5 ± 8.6 | −8 |
| S(−)HA-966 | Veh. | 102.6 ± 4.6 | — | 152.6 ± 5.5 | — |
| | 1.0 | 96.8 ± 2.2 | −5 | 155.0 ± 3.7 | +2 |
| | 3.0 | 85.5 ± 4.7 | −17 | 118.6 ± 4.4 | −22 |
| | 10.0 | 18.8 ± 7.0 | −82 | 15.5 ± 5.3 | −90 |
| Diazepam | Veh. | 96.8 ± 3.4 | — | 157.8 ± 5.0 | — |
| | 0.3 | 106.7 ± 4.8 | +10 | 139.8 ± 6.9 | −12 |
| | 1.0 | 125.2 ± 4.9 | +29 | 145.0 ± 9.0 | −10 |
| | 3.0 | 136.0 ± 6.2 | +40 | 104.5 ± 9.2 | −37 |

TABLE 3

Elevated Plus Maze

The effects of (±)HA-966, R(+)HA-966, S(−)HA-966 and diazepam in the elevated plus maze. Rats were administered (mg/kg, i.p.) compounds 30 minutes prior to testing. Open arm exploration time was measured in seconds (mean±S.E.) for 5 minutes. Motor activity was measured by the number of arm crossings (mean±S.E.) N=8 animals per group.

RESULTS

In all three assays, R(+)HA-966 compared favorably with diazepam without significantly affecting motor activity.

TABLE 3

| | | ELEVATED PLUS MAZE | | | |
|---|---|---|---|---|---|
| Compound | Dose (mg/kg) | Open Arm Activity X ± S.E. (s) | % Change | Motor Activity X ± S.E. (Arm Crossing) | % Change |
| R(+)HA-966 | Veh. | 44.2 ± 6.7 | — | 11.2 ± 0.7 | — |
| | 1.0 | 50.8 ± 4.7 | +15 | 10.0 ± 0.7 | −11 |
| | 3.0 | 77.7 ± 5.8 | +76 | 10.8 ± 1.1 | −3 |
| | 10.0 | 70.8 ± 6.3 | +60 | 11.8 ± 0.6 | +6 |
| (±)HA-966 | Veh. | 49.8 ± 4.3 | — | 11.1 ± 0.6 | — |
| | 0.3 | 48.0 ± 4.2 | −4 | 11.1 ± 0.7 | +0 |
| | 1.0 | 73.0 ± 7.0 | +46 | 11.3 ± 0.5 | +2 |
| | 3.0 | 79.1 ± 6.3 | +59 | 8.6 ± 0.4 | −23 |
| S(−)HA-966 | Veh. | 44.2 ± 6.7 | — | 11.2 ± 0.7 | — |
| | 1.0 | 38.8 ± 7.0 | −12 | 10.2 ± 0.8 | −9 |
| | 3.0 | 37.0 ± 6.5 | −16 | 4.2 ± 0.6 | −63 |
| | 10.0 | ND | | ND | |
| Diazepam | Veh. | 50.0 ± 6.7 | — | 9.3 ± 1.1 | — |
| | 0.3 | 50.3 ± 3.9 | +1 | 9.0 ± 0.6 | −3 |
| | 1.0 | 79.3 ± 4.7 | +59 | 10.0 ± 0.9 | +7 |
| | 3.0 | 72.2 ± 8.4 | +44 | 7.8 ± 0.4 | −16 |

ND = not determined

What is claimed is:

1. A method of treating anxiety in a patient requiring said treatment which comprises administering to said patient an effective anxiety treating amount of R(+)-3-amino-1-hydroxy-pyrrolidin-2-one.

2. The method of claim 1 wherein the amount of said compound administered is 0.1 to 1.5 mg/kg of body weight per day.

* * * * *